United States Patent [19]

Scharnberg

[11] Patent Number: 5,148,805
[45] Date of Patent: Sep. 22, 1992

[54] DEFIBRILLATOR PAD SYSTEM AND METHOD FOR USING SAME

[75] Inventor: Lorne C. Scharnberg, West Des Moines, Iowa

[73] Assignee: Kas Products, Inc., Des Moines, Iowa

[21] Appl. No.: 653,360

[22] Filed: Feb. 11, 1991

[51] Int. Cl.$^5$ .............................................. A61N 1/04
[52] U.S. Cl. ................... 128/419 D; 128/640; 128/798
[58] Field of Search .................... 128/419 D, 640, 798

[56] References Cited

U.S. PATENT DOCUMENTS

| | | | |
|---|---|---|---|
| 4,243,051 | 1/1981 | Wittemann | 128/798 |
| 4,610,254 | 9/1986 | Morgan et al. | 128/419 D |
| 4,736,752 | 4/1988 | Munck et al. | 128/798 |

Primary Examiner—William E. Kamm
Assistant Examiner—Scott M. Getzow
Attorney, Agent, or Firm—Zarley, McKee, Thomte, Voorhees, & Sease

[57] ABSTRACT

The defibrillator pad system of the present invention includes a pair of pads which can be adhered to electrodes of defibrillator paddles. Wires are connected to these pads and lead to two separate electrode pads which are adapted to be attached to the patient's chest. The defibrillator paddles can thus be used to defibrillate the patient while the defibrillator paddles are remote from the patient. A pair of plug members are provided between the two pairs of pads so that they can be disconnected from one another.

10 Claims, 2 Drawing Sheets

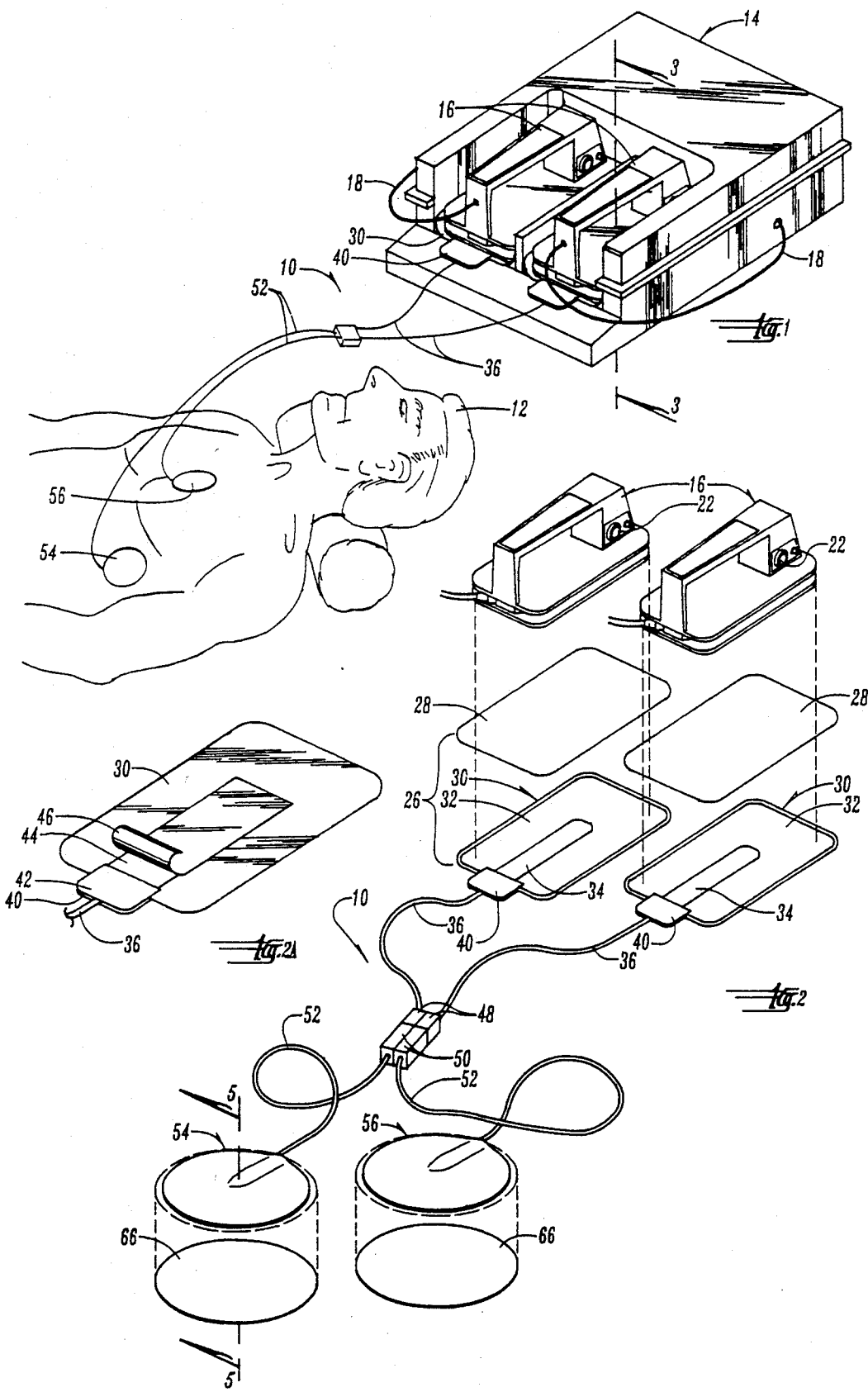

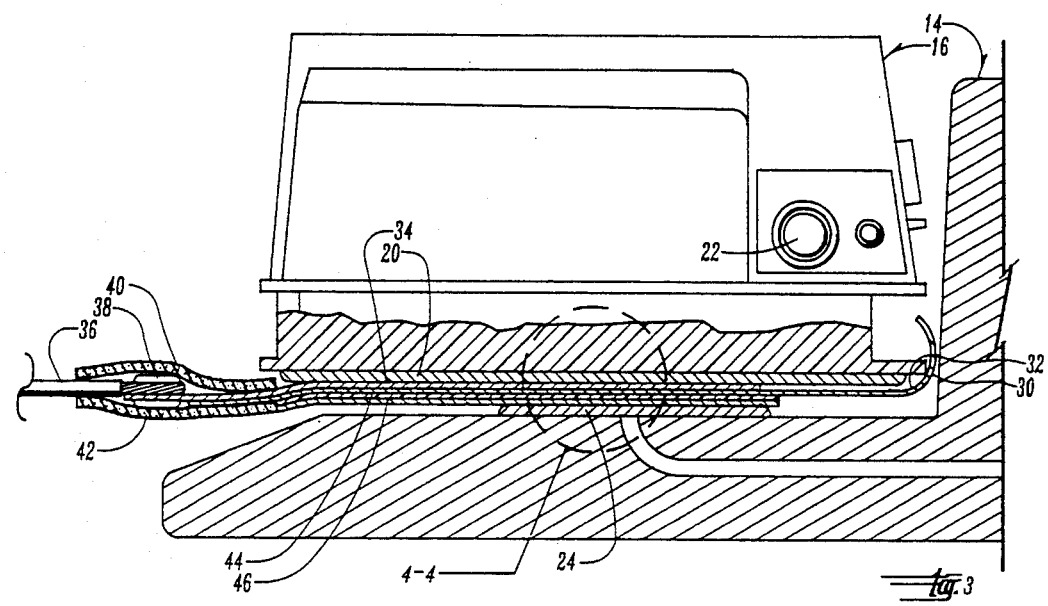
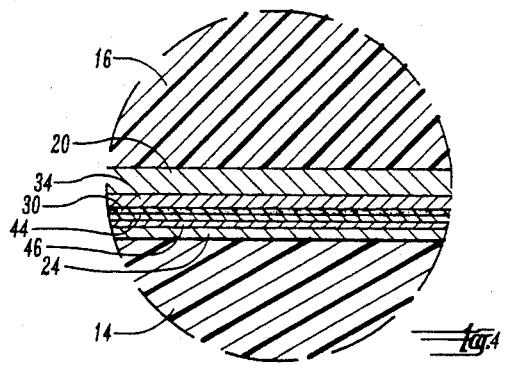
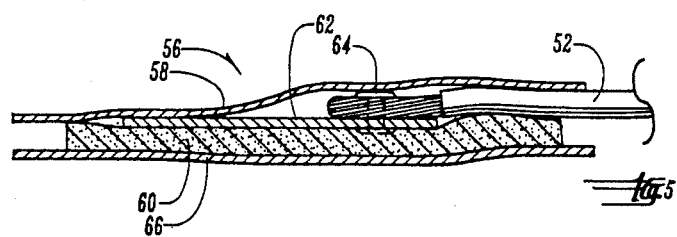

DEFIBRILLATOR PAD SYSTEM AND METHOD FOR USING SAME

BACKGROUND OF THE INVENTION

This invention relates to a defibrillator pad system and a method for using same.

Defibrillation is a process used for patients encountering fibrillation of the heart. The defibrillation process usually involves placing two electrode paddles on the patient's chest and applying a high density electrical current to the patient so as to stimulate the heart and correct the fibrillation of the heart.

Dry skin on a patient causes the interface between the metal defibrillator paddles and the skin of the patient to have a high impedance. This can cause severe skin burns and may cause significant reduction in the current delivered to the heart so as to prevent successful defibrillation.

Present methods for applying the defibrillator paddles to the skin involve the use of electrically conductive gels which are applied to the patient's skin and which are also applied to the defibrillator paddles. Often the gel is incompletely applied, leaving bare spots between the paddle and the patient's skin. These bare spots may result in burning of the patient's skin during the discharge. Also, it is necessary for the users of the paddles to continue to apply pressure between the paddle and the patient's skin in order to ensure a positive electrical contact therebetween.

Another disadvantage of presently used gels is that they are messy. The gel sometimes gets on the user's hands and arms, making it difficult for the user to perform other functions such as cardiopulmonary resuscitation.

Another presently used method for defibrillating involves the use of moisturized polymer pads which are enclosed within an airtight envelope. The pads are removed from the envelope and placed on the patient's chest immediately prior to use. Then the defibrillator paddles are placed over the pads in preparation for their use. The disadvantage of these moisturized pads is that they tend to harden and become brittle after prolonged exposure to the atmosphere. Furthermore, they do not provide a strong adhesive bond between the pad and the patient's chest, and therefore, they sometimes slip or move after use.

Another method for defibrillating involves the use of a pad such as disclosed in U.S. Pat. No. 4,779,630. The method disclosed in this patent shows a polymer pad which is tacky and adhesive in its characteristics. It is also a good electrical conductor. The polymer pad is placed over the electrode on the defibrillator paddle. Then the paddle with the polymer pad thereon is placed over the patient's chest. The tackiness of the polymer pad causes the defibrillator paddle to adhere to the pad and also causes the polymer pad to adhere to the patient's chest, thereby providing a good electrical contact between the paddle and the chest.

All of the above processes involve applying the defibrillator paddle directly to the patient's chest. This is sometimes difficult to do reliably in ambulances or in helicopters due to the jostling and movement of the patient during transporting.

Therefore, a primary object of the present invention is the provision of an improved defibrillator pad system and method for using same.

A further object of the present invention is the provision of an improved defibrillator pad system which permits electrode pads to be attached to the patient's skin and which includes flexible connector leading from the electrode pads to the defibrillator paddles.

A further object of the present invention is the provision of an improved defibrillator pad system which permits the monitoring of the patient's heart through the defibrillator paddles.

A further object of the present invention is the provision of an improved defibrillator pad system which permits the preapplication of the pad system to the defibrillator paddles in a nonemergency setting.

A further object of the present invention is the provision of an improved defibrillator paddle sizes and shapes.

A further object of the present invention is the provision of a defibrillator pad system which is economical to manufacture, durable in use, and efficient in operation.

SUMMARY OF THE INVENTION

The present invention utilizes a pair of first pad members, each of which is adapted to be attached to the electrode surfaces of the defibrillator paddles. The first pad members include a first sheet member having an upper and lower surface and having a first electrically conductive member operatively secured to the upper surface thereof. The first electrically conductive member has a surface area less than that of the electrodes surfaces of the defibrillator paddles, and the first sheet member is sufficiently large to be greater than the surface area of the defibrillator paddles. The upper surface of the first sheet member is tacky so that it will adhere to the electrode surface of the defibrillator paddle.

When the first pad members are adhered to the defibrillator paddles, the tacky surface of the first sheet members causes them to adhere to the electrode surfaces of the defibrillator paddles, and causes them to hold the first conductive members of the first pad members in electrical contact with the electrode surfaces of the defibrillator paddles.

A pair of second pad members each comprises a second sheet member and an electrically conductive member attached to the lower surface thereof. The second pad members are adapted to adhere to the surface of the patient's skin on the patient's chest.

A pair of flexible electrical connectors innerconnect the first pad members with the second pad members so as to provide electrical continuity therebetween.

In operation, the first pad members are applied to the electrode surfaces of the defibrillator paddles. When it is desired to defibrillate a patient, the second pad members are adhered to the patient's chest at the desired locations for defibrillation. The flexible electrical connectors provide electrical continuity between the second pad members on the patient's chest and the first pad members on the defibrillator paddle electrodes.

The defibrillator paddles are then actuated to cause an electrical charge to be delivered to the second pad members on the patient's chest.

It is also possible to utilize the present system for monitoring the patient's heart performance. The system is adhered to the patient's chest and the defibrillator paddles, and the defibrillator paddles are connected to a heart monitoring system. The second pad members sense the performance characteristics of the heart and transform these characteristics into electrical signals which are transmitted back through the paddles to the heart monitoring system.

The electrical connectors between the first and second pad members can optionally include a plug located intermediate their lengths so that each of the connectors can be separated into two segments. This permits the application of the first pad members to the defibrillator paddles prior to an emergency situation where defibrillation is needed. When defibrillation is needed, the second paddles can be adhered to the patient's chest, and the plugs connected so as to provide electrical continuity between the second pads and the defibrillator paddles.

BRIEF DESCRIPTION OF THE DRAWINGS

FIG. 1 is a perspective view of the defibrillator pad system of the present invention.

FIG. 2 is an exploded perspective view of the defibrillator pad system of the present invention.

FIG. 2a shows the undersurface of the sheet member.

FIG. 3 is a sectional view taken along line 3—3 of FIG. 1.

FIG. 4 is an enlarged detailed sectional view taken along line 4—4 of FIG. 3.

FIG. 5 is an enlarged sectional view taken along line 5—5 of FIG. 2.

DESCRIPTION OF THE PREFERRED EMBODIMENT

Referring to the drawings, the numeral 10 generally refers to the defibrillator pad system of the present invention. System 10 is adapted for use to defibrillate a patient 12 utilizing a defibrillator console 14 having defibrillator paddles 16 associated therewith. The paddles 16 are connected to the console by means of cords 18. Each defibrillator paddle includes an electrode 20 having a downwardly presented flat surface. The electrode can be actuated by means of actuation button 22 so as to introduce a high voltage electrical charge to the paddle electrode 20. The defibrillator paddles 16 rest on the console 14 with their electrode surfaces 20 in electrical contact with a pair of paddle testing contacts 24. These contacts 24 permit the testing of the defibrillator paddles. When the button 22 is actuated with the electrode 20 in contact with the testing contacts 24, it is possible to test the device to make certain that it is working properly.

Detachably mounted to the surfaces of electrodes 20 are a pair of first pad assemblies designated generally by the numeral 26. Each pad assembly 26 comprises a release liner 28, a first plastic sheet member 30 having an upwardly presented surface 32 provided with an adhesive tacky substance. Also mounted on the upper surface of each plastic sheet member 30 is a conductor member 34 preferably made from conductive stainless steel foil or some other good electrical conductor. The foil 34 is in a shape which is substantially smaller than the shape of the smaller in length and width than the size of the sheet member 30 so as to expose a large portion of the adhesive tacky substance on the upper surface of the sheet member 30. The release liner 28 is larger than the sheet member 30 and fits in covering relation over the upper surface of sheet member 30 so as to protect the adhesive substance thereon.

An electric wire or cord 36 is electrically connected to the foil 34 by means of a rivet 38. A pair of plastic foam cover tabs 40, 42 are operatively secured by adhesive or the like in covering relation over the rivet 38 so as to protect the connection between the wire and the foil.

FIG. 2a illustrates the undersurface of the sheet member 32 and shows a Mylar tape 44 attached thereto. A paper instruction label is adhered in covering relation over the Mylar tape 44. The purpose of the Mylar tape 44 is to protect the sheet member from tearing when it is placed in contact over the paddle testing contacts in console 14 as illustrated in FIG. 3.

The first pad assemblies 26 are used by removing the release liners 28 and by placing the upper tacky surfaces 32 of sheet members 30 in covering engagement over the electrode 20 of each paddle 16. The size of the sheet members 30 is greater than the electrodes 20 so as to provide complete covering protection over the electrode 20. The paddle can then be placed on the console in the position shown in FIGS. 1 and 3, whereby the sheet member 30 protects the electrode 20 from electrical contact with outside sources. However, the foil member 34 is held in electrical contact with the electrode 20 by means of the adhesive on the upper surface of sheet member 30.

The end of cord 36 is provided with a plug member 48, and a second cord 52 is provided with a plug member 50 which is adapted to be connected to the plug member 48.

A pair of patient electrodes 54, 56 are connected to the other ends of cords 52 and are adapted to be placed on the patient's chest for defibrillating in the manner shown in FIG. 1.

The structure of patient electrodes 54 may vary, and there are a number of such electrodes which are commercially available. A preferred form of electrode is shown in FIG. 5 which contains an upper sheet member 58, and a lower polymer sheet member 60 adhered thereto. Interposed between sheet members 58, 60 is a foil sheet 62 which is riveted to the end of wire 52 by means of a rivet 64. The polymer sheet member 60 is a flexible polymer material which is also an electrical conductor and which has a tacky consistency so that it can detachably adhere to the surface of the patient's skin. An example of such a conductive polymer is manufactured by Promeon Division of Medtronics, Inc., 6951 Central Avenue, N.E., Minneapolis, Minn. 55440 under the product designation RG 63 B, or RG 63 T, the latter being the preferred polymer. The conductive polymer includes thin fibers of polyethylene scrim which run through the polymer and which give the polymer sheet strength. The scrim may also be made of other materials, such as carbon, nickel-coated carbon, or other materials. A release liner 66 is provided in covering relation over the polymer sheet member 60 so as to protect it until it is ready for use.

The method of using the present invention is as follows. Prior to defibrillation of the patient, the first sheet members 26 are attached to the electrodes 20 of the paddles 16. This is done by removing the release liners 28 and by placing the upper tacky surfaces 32 of the sheet members 30 in facing engagement with the electrodes 20 of the paddles 16. The paddles 16 can then be placed in the console 14 as shown in FIG. 1 and FIG. 3. If desired, the plugs 48, 50 can be disconnected until such time as the defibrillation of the patient may be necessary.

When an emergency arises where defibrillation is necessary, the pads 54, 56 are removed from their packaging and the release liners 66 are removed. The pads 54, 56 are then placed on the patient's chest at the desired location. The tacky characteristic of the polymer sheet member 60 causes the pads 54, 56 to adhere to the patient's skin and provide a good electrical contact therewith. The plugs 48, 50 are then connected as shown in FIG. 1, and the patient is ready for defibrillating. Defibrillation is accomplished merely by pressing the actuation button 22 on the paddles 16 while the paddles are remote from the patient. The charge is carried through the cords 36, 52 to the electrodes 54, 56 for defibrillating the patient.

It is also possible to use the present invention for monitoring the patient during transporting to a hospital. The electrodes 54, 56 are retained in place as shown in FIG. 1. Many defibrillator consoles include in their circuitry means for monitoring the patient when the paddles 16 are in electrical contact with the patient. This can be accomplished without having to attach the paddles 16 themselves to the patient because the present invention permits electrical continuity to be maintained merely by means of the electrodes 54, 56. If defibrillation is needed suddenly during transporting, all that is necessary is to actuate the paddles 16.

From the foregoing, it can be seen that the present invention provides many advantages. The first pad assemblies 26 can be mounted on the paddles prior to any emergency situation so that they are ready for operation in the event an emergency arises. Good electrical contact is maintained between the skin of the patient's chest and the defibrillator paddles, and repeated defibrillations can be accomplished as needed. The device also can be used for monitoring as explained above. Thus, it can be seen that the present invention accomplishes at least all of its stated objectives.

I claim:

1. A method for using a defibrillator pad system with a pair of defibrillator paddles, each of said paddles having an electrode surface, said defibrillator pad system comprising a pair of first pad members, each comprising a first sheet member having upper and lower surfaces and a first electrically conductive member operatively secured to said upper surface of said first sheet member, said first electrically conductive member having a surface area less than the surface area of said electrode surfaces of each of said defibrillator paddles, said upper surface of said first sheet member being tacky so as to adhere to said electrode surfaces and having a surface area greater than said electrode surfaces of each of said defibrillator paddles; a pair of elongated flexible electrical connectors each having first and second opposite ends; a pair of second pad members, each comprising a second sheet member having an upper and a lower surface, an electrically second conductive member attached to said lower surface of said second sheet member, at least one of said second conductive member and said lower surface of said second sheet member being tacky so as to readily adhere to a patient's skin and hold said second conductive member in electrical contact therewith; first securing means electrically connecting said first ends of connectors to said first electrically conductive members of said first pad members; second securing means electrically connecting said second ends of said connectors to said second conductive members of said second pad members, said method comprising:

placing said upper surfaces of said pair of first pad members and said first electrically conductive members in facing engagement with said electrode surfaces of said defibrillator paddles whereby said tackiness of said upper surfaces of said first sheet members will secure said upper surfaces of said first sheet members in covering relation over said electrode surfaces and will hold said first conductive members in electrical contact with said electrode surfaces;

placing said lower surfaces of said second sheet members and said second conductive members in facing contact with a patient's skin at desired locations for defibrillating said patient's heart, whereby said tackiness of said one of said second conductive members and said lower surfaces of said second sheet members causes said second pad members to be secured to said patient's skin at said desired locations with said second conductive members being in electrical contact with said patient's skin at said locations.

2. A method according to claim 1 and further comprising actuating said defibrillator paddles while said defibrillator paddles are remote from said patient's skin to cause an electrical charge to be delivered through said pad system to said patient's skin for defibrillating said patient.

3. A method according to claim 1 and further comprising connecting said defibrillator paddles to a heart monitoring system whereby said second conductive members will create electrical signals responsive to, and having characteristics correlating to, said patient's heart performance, and said signals will be carried through said pad system to said defibrillator paddles and then to said heart monitoring system for monitoring said performance of said patient's heart.

4. A defibrillator pad system for use with a pair of defibrillator paddles, each of said paddles having an electrode surface, said pad system comprising:

a pair of first pad members, each comprising a first sheet member having upper and lower surfaces and a first electrically conductive member operatively secured to said upper surface of said first sheet member, said first electrically conductive member having a surface area less than the surface area of said electrode surfaces of each of said defibrillator, paddles, said upper surface of said first sheet member having a tacky characteristic to enable it to said electrode surfaces and having a surface area greater than said electrode surfaces of each of said defibrillator paddles whereby said pair of first pad members may be attached in covering relation over said electrode surfaces of said defibrillator paddles with said tacky characteristic of said upper surfaces of said first sheet members causing said upper surfaces of said first sheet members to adhere to said electrode surfaces so as to hold said first conductive members in electrical contact with said electrode surfaces of said defibrillator paddles;

a pair of elongated flexible electrical connectors each having first and second opposite ends;

a pair of second pad members, each comprising a second sheet member having an upper and a lower surface, an electrically second conductive member attached to said lower surface of said second sheet member, at least one of said second conductive member and said lower surface of said second sheet member having a tacky characteristic to enable it to readily adhere to a patient's skin and hold said second conductive member in electrical contact therewith;

first securing means electrically connecting said first ends of connectors to said first electrically conductive members of said first pad members;

second securing means electrically connecting said second ends of said connectors to said second conductive members of said second pad members.

5. A defibrillator pad system according to claim 4 wherein each of said electrical connectors is comprised of first and second segments, coupling means detachably securing and electrically connecting said first and second segments together.

6. A defibrillator pad system according to claim 4 wherein said second conductive members are comprised of an electrically conductive polymer having a tacky characteristic capable of detachably adhering to a patient's skin.

7. A defibrillator pad system for use with a pair of defibrillator paddles, each of said paddles having an electrode surface, said pad system comprising:

a pair of first pad members, each comprising a first electrically insulative sheet member having upper and lower surfaces and a first electrically conductive member operatively secured to said upper surface of said first sheet member, said first electrically conductive member having a surface area less than the surface area of said electrode surfaces of each of said defibrillator paddles, said upper surface of said first sheet member having a tacky characteristic to enable it to adhere to said electrode surfaces and having a surface area greater than said electrode surfaces of each of said defibrillator paddles whereby said pair of first pad members may be attached in covering relation over said electrode surfaces, of said defibrillator paddles with said tacky characteristic of said upper surfaces of said first sheet members causing said upper surfaces of said first sheet members to adhere to said electrode surfaces so as to hold said first conductive members in electrical contact with said electrode surfaces of said defibrillator paddles;

a pair of elongated flexible electrical connectors each having first and second opposite ends;

first securing means electrically connecting said first ends of connectors to said first electrically conductive members of said first pad members.

8. A defibrillator pad system according to claim 7 comprising a first coupling means connected to said second ends of said pair of connectors.

9. A defibrillator pad system according to claim 8 comprising a second pair of flexible connectors having first and second ends, second coupling means on said second ends of said second pair of connectors and being detachably coupled to said first coupling means.

10. A defibrillator pad system according to claim 9 and further comprising a pair of second pad members each connected to said first ends of one of said second pair of connectors, said second pad members comprising an electrically conductive member in electrical connection with said second pair of connectors.

* * * * *

UNITED STATES PATENT AND TRADEMARK OFFICE
CERTIFICATE OF CORRECTION

PATENT NO. : 5,148,805
DATED : September 22, 1992
INVENTOR(S) : Scharnberg, Lorne C.

It is certified that error appears in the above-indentified patent and that said Letters Patent is hereby corrected as shown below:

Column 6, line 44, Claim 4, after "enable it" insert --to adhere--.

Signed and Sealed this

Twenty-eighth Day of December, 1993

Attest:

BRUCE LEHMAN

Attesting Officer     Commissioner of Patents and Trademarks